United States Patent
Nakao et al.

(10) Patent No.: US 9,120,098 B2
(45) Date of Patent: *Sep. 1, 2015

(54) FLUID HANDLING DEVICE AND FLUID HANDLING SYSTEM

(75) Inventors: Tomoki Nakao, Saitama (JP); Koichi Ono, Saitama (JP)

(73) Assignee: Enplas Corporation, Saitama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/110,086

(22) PCT Filed: Mar. 12, 2012

(86) PCT No.: PCT/JP2012/001690
§ 371 (c)(1),
(2), (4) Date: Oct. 4, 2013

(87) PCT Pub. No.: WO2012/137413
PCT Pub. Date: Oct. 11, 2012

(65) Prior Publication Data
US 2014/0023566 A1    Jan. 23, 2014

(30) Foreign Application Priority Data

Apr. 4, 2011 (JP) ................................ 2011-082820

(51) Int. Cl.
*B01L 3/00* (2006.01)
*G01N 27/00* (2006.01)
*B01J 19/00* (2006.01)
(Continued)

(52) U.S. Cl.
CPC .............. *B01L 3/56* (2013.01); *B01J 19/0093* (2013.01); *B01L 3/502707* (2013.01); *B81C 3/001* (2013.01); *B01J 2219/00783* (2013.01); *B01J 2219/00808* (2013.01); *B01J 2219/00833* (2013.01); *B01J 2219/00853* (2013.01); *B01J 2219/00988* (2013.01); *B01L 3/502715* (2013.01); *B01L 7/525* (2013.01); *B01L 2200/0689* (2013.01); *B01L 2300/0645* (2013.01); *B01L 2300/0816* (2013.01); *B01L 2300/0887* (2013.01); *B01L 2300/1827* (2013.01); *B01L 2400/0406* (2013.01); *B01L 2400/0421* (2013.01); *B29C 65/4855* (2013.01); *B29C 66/112* (2013.01); *B29C 66/114* (2013.01); *B29C 66/53461* (2013.01); *B29C 66/71* (2013.01); *B29C 66/7352* (2013.01); *B29K 2707/04* (2013.01); *B29L 2031/756* (2013.01); *G01N 27/403* (2013.01); *G01N 27/44704* (2013.01); *G01N 27/44791* (2013.01)

(58) Field of Classification Search
None
See application file for complete search history.

(56) References Cited

U.S. PATENT DOCUMENTS

| 6,939,451 B2 | 9/2005 | Zhao et al. |
| 2002/0110492 A1 * | 8/2002 | Handique ..................... 422/100 |

(Continued)

FOREIGN PATENT DOCUMENTS

| JP | 2006-142198 A | 6/2006 |
| JP | 2006-517652 A | 7/2006 |

*Primary Examiner* — Jennifer Wecker
(74) *Attorney, Agent, or Firm* — Brundidge & Stanger, P.C.

(57) ABSTRACT

The present invention relates to a microchannel chip capable of preventing fluid leakage caused by a lamination defect. Bottomed first regions, second regions, and third regions are formed by joining a film to a lower surface of the chip main body of a microchannel chip. The third regions are in communication with the second regions and are formed on carbon inks. The third regions are formed wider than the carbon inks are. The third regions are filled with an electroconductive adhesive.

3 Claims, 6 Drawing Sheets

(51) Int. Cl.
   *B81C 3/00* (2006.01)
   *B01L 7/00* (2006.01)
   *F16L 53/00* (2006.01)
   *G01N 27/403* (2006.01)
   *G01N 27/447* (2006.01)
   *B29C 65/00* (2006.01)
   *B29L 31/00* (2006.01)
   *B29K 707/04* (2006.01)
   *B29C 65/48* (2006.01)

(56) References Cited

U.S. PATENT DOCUMENTS

| | | | |
|---|---|---|---|
| 2004/0189311 | A1 | 9/2004 | Glezer et al. |
| 2004/0241381 | A1* | 12/2004 | Chen .............................. 428/66.6 |
| 2007/0102293 | A1* | 5/2007 | Tai et al. ........................ 204/409 |
| 2007/0286773 | A1* | 12/2007 | Schlautmann et al. ...... 422/68.1 |
| 2009/0065357 | A1 | 3/2009 | Glezer et al. |
| 2009/0066339 | A1 | 3/2009 | Glezer et al. |
| 2011/0052446 | A1* | 3/2011 | Hirano et al. ................. 422/68.1 |

\* cited by examiner

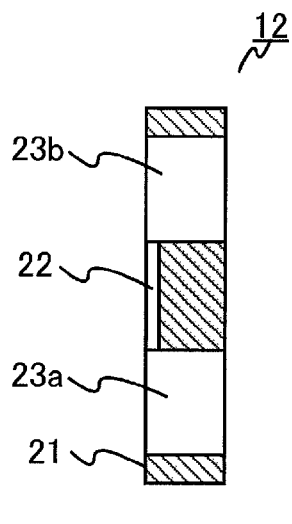
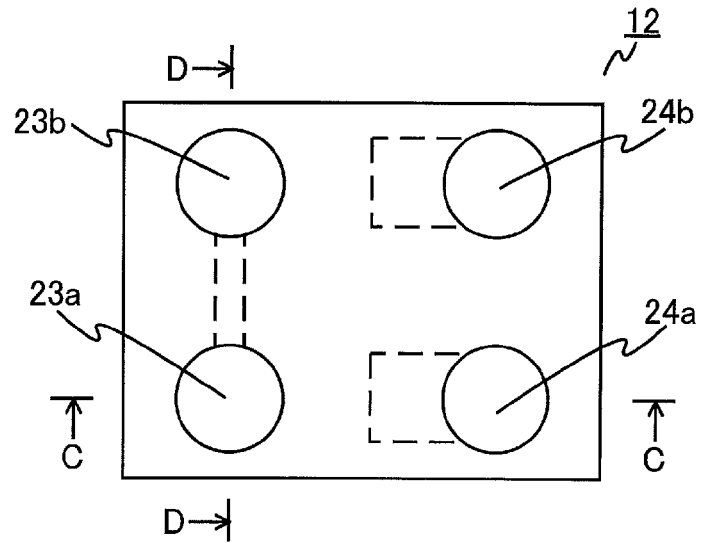
FIG. 2D
FIG. 2A
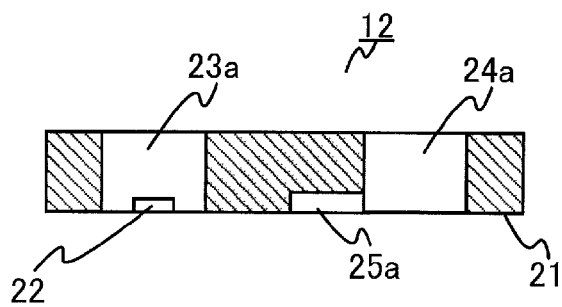
FIG. 2B
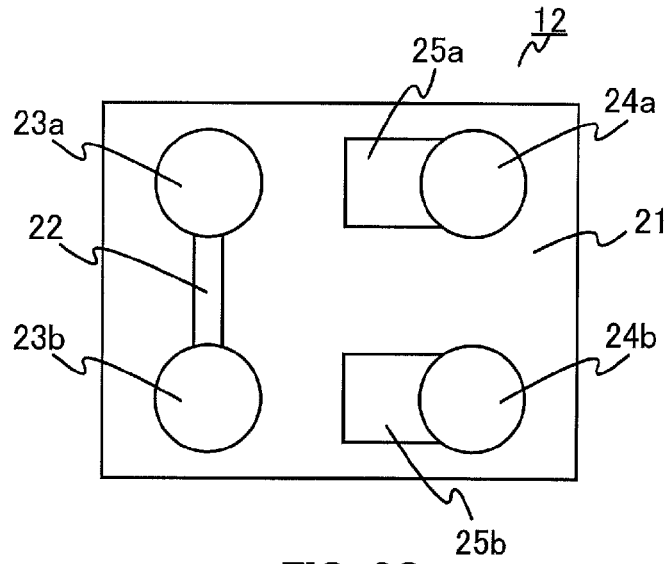
FIG. 2C

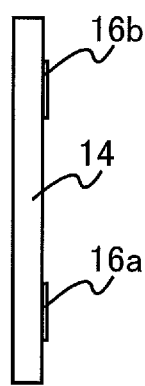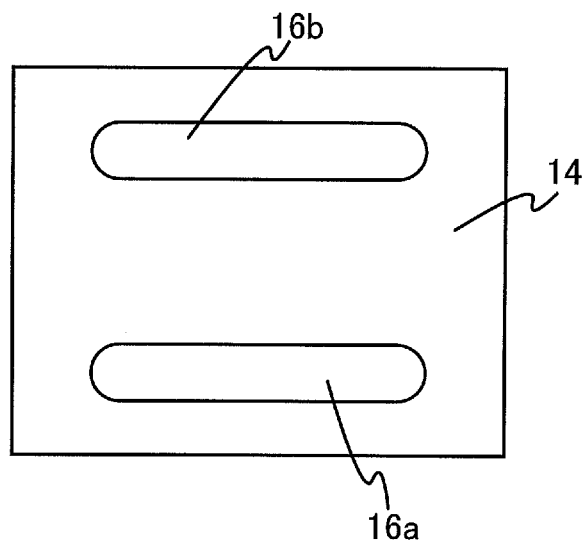
FIG. 3C
FIG. 3A
FIG. 3B

FLUID HANDLING DEVICE AND FLUID HANDLING SYSTEM

TECHNICAL FIELD

The present invention relates to a fluid handling apparatus used for analysis, treatment or the like of a liquid sample and a fluid handling system including the same.

BACKGROUND ART

In recent years, micro-analytical systems are used to carry out an inspection/analysis of trace substances such as proteins and nucleic acids (e.g., DNA) accurately and at high speed in the scientific field such as biochemistry and analytical chemistry or in the medical field.

As an example of the micro-analytical system, there is a system which fills a channel formed on a micro-channel chip with a buffer solution, injects a sample through an injection port connected to the channel, applies a voltage to both ends of the channel and electrophoreses the sample to conduct an analysis.

The micro-channel chip is manufactured by joining a film (thin film) or thin plate to a chip body in which the channel is formed. A reservoir into which a liquid is injected is formed at both ends of the channel, and an electrode is formed in each reservoir. As an example of an electrode forming method, a method in which an electrode pattern is printed on a film or thin plate with a carbon ink is known (see PTL 1). One end of the electrode pattern formed in this manner is formed so as to be located inside the reservoir and the other end thereof is formed so as to be located outside the reservoir. The micro-channel chip is configured so that the electrode of the electrophoresis apparatus is made to contact the other end of the electrode pattern and a voltage can be applied to the liquid sample without contacting the liquid sample injected into the reservoir.

CITATION LIST

Patent Literature

PTL 1
U.S. Pat. No. 6,939,451

SUMMARY OF INVENTION

Technical Problem

According to the above electrode forming method, the periphery of the carbon ink layer in the film or thin plate may remain unbonded (insufficiently laminated) to the chip body due to the thickness of the carbon ink, and thus, the liquid may leak.

However, the background art adopts no measures for this liquid leakage, and the liquid leakage may cause contamination of the electrophoresis apparatus (electrode).

It is an object of the present invention to provide a fluid handling apparatus and a fluid handling system capable of preventing a liquid from leaking from the fluid handling apparatus such as a micro-channel chip and preventing contamination of an external environment.

Solution to Problem

According to an aspect of the present invention, there is provided a fluid handling apparatus including: a substrate member where a groove or a through hole is formed; a cover member that is bonded to one surface of the substrate member and has a thin film shape or a thin plate shape; and a transfer function section that is formed in a laminated shape to cover a part of a surface of the cover member on the side of the substrate member and transfers electricity or heat, wherein a groove or a through hole that forms a first region is formed in a portion of the substrate member corresponding to one end of the transfer function section, an opening of the groove or the through hole that forms the first region on the side of the cover member is closed by the cover member, a second region that communicates with an outside is formed in a portion of the substrate member corresponding to the other end of the transfer function section, the transfer function section electrically or thermally connects the first region and the second region to each other, a groove that forms a third region is formed in a portion of the substrate member corresponding to a portion between one end and the other end of the transfer function section to extend over edges of the transfer function section, an opening of the groove that forms the third region on the side of the cover member is closed by the cover member, and the third region communicates with the second region and is filled with an adhesive.

According to another aspect of the present invention, there is provided a fluid handling system including the fluid handling apparatus.

Advantageous Effects of Invention

According to the present invention, the groove is formed in the substrate member, and a space (third region) formed by closing the groove with the thin film or thin plate is filled with the adhesive. Accordingly, it is possible to prevent leakage of a liquid leaked through a gap between the substrate member and the cover member produced due to the thickness of the transfer function section of the laminated shape, and to prevent contamination of an external environment.

BRIEF DESCRIPTION OF DRAWINGS

FIG. 2A to FIG. 2D are diagrams illustrating the shape of a chip body of the micro-channel chip shown in FIG. 1A to FIG. 1D;

FIG. 3A to FIG. 3C are diagrams illustrating the shape of a film after carbon ink printing of the micro-channel chip shown in FIG. 1 to FIG. 1D;

DESCRIPTION OF EMBODIMENTS

Hereinafter, an embodiment of the present invention will be described in detail with reference to the accompanying drawings.

Configuration of Micro-Channel Chip

Figure 1D:
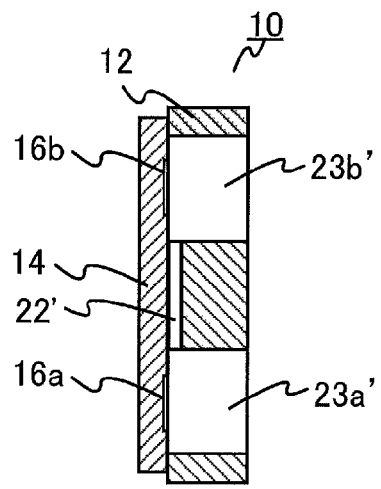
FIG. 1A to FIG. 1D are diagrams illustrating the shape of a micro-channel chip according to an embodiment of the present invention.
Figure 1A:
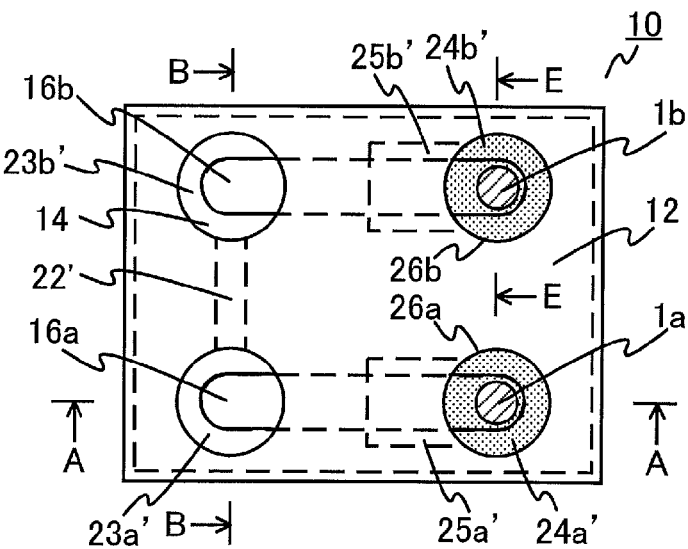
Figure 1B:
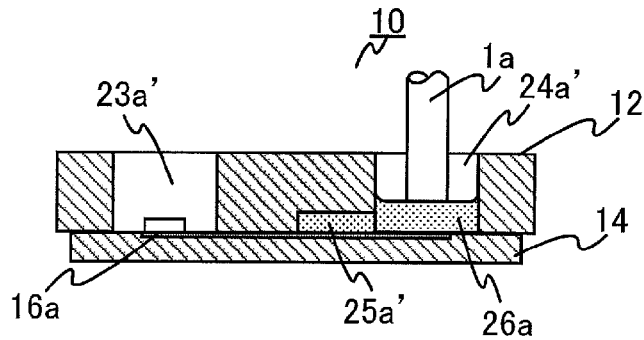
Figure 1C:
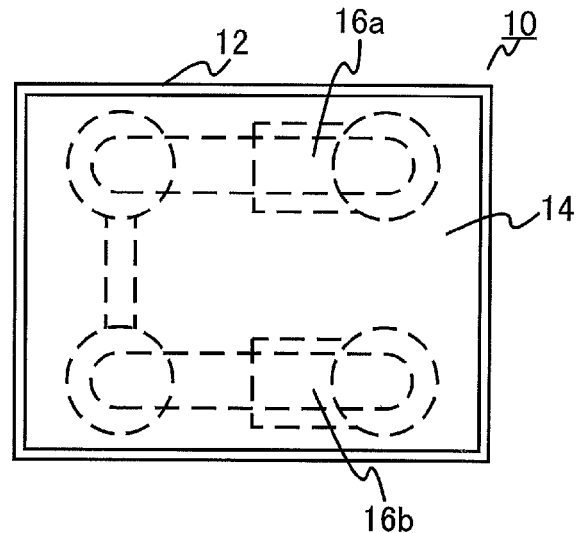

FIG. 1A to FIG. 1D are diagrams illustrating the shape of a micro-channel chip as a fluid handling apparatus according to the present embodiment. FIG. 1A is a plan view, FIG. 1B is a front cross-sectional view along line A-A, FIG. 1C is a bottom view, and FIG. 1D is a left side cross-sectional view along line B-B. FIG. 1A and FIG. 1B also show electrode rods 1a and 1b together.

As shown in FIG. 1A to FIG. 1D, micro-channel chip 10 includes transparent chip body (substrate member) 12 that is an approximately rectangular flat plate, film (cover member) 14, and carbon inks (electrodes as transfer function sections) 16a and 16b.

The thickness of chip body 12 is approximately 1 mm, the thickness of film 14 is approximately 100 μm, and the thickness of carbon inks 16a and 16b is approximately 10 μm.

Chip body 12 and film 14 are formed of a resin material such as polyethylene terephthalate, polycarbonate, polymethylmethacrylate, vinyl chloride, polypropylene, polyether or polyethylene. Different materials may also be used for chip body 12 and film 14.

Carbon inks 16a and 16b are printed on film 14. Film 14 is bonded to chip body 12 by adhesion using an organic adhesive or thermo compression bonding.

FIG. 2A to FIG. 2D are diagrams illustrating the shape of chip body 12. FIG. 2A is a plan view, FIG. 2B is a front cross-sectional view along line C-C, FIG. 2C is a bottom view, and FIG. 2D is a left side cross-sectional view along line D-D.

Elongated micro-groove 22 is formed on undersurface 21 of chip body 12, which is a surface that faces film 14. Micro-groove 22 has a substantially rectangular cross section having a length (width and depth) per side of the order of several tens of micrometers. In a state where chip body 12 and film 14 are bonded together, channel 22' is formed as the opening of micro-groove 22 is closed by film 14.

Through holes 23a and 23b which are open outward, having an approximately circular cross section are formed at both ends of each micro-groove 22 of chip body 12. The diameter of through holes 23a and 23b is several hundreds of micrometers to several millimeters. In a state where chip body 12 and film 14 are bonded together, bottomed first regions 23a' and 23b' having functions as an injection port and an exhaust port of a buffer solution and a sample are formed as openings of through holes 23a and 23b are closed by film 14.

Through holes 24a and 24b having an approximately circular cross section are formed in chip body 12. The diameter of through holes 24a and 24b is several hundreds of micrometers to several millimeters. In a state where chip body 12 and film 14 are bonded together, bottomed second regions 24a' and 24b' having a function of insertion ports of electrode rods 1a and 1b are formed as openings of through holes 24a and 24b are closed by film 14.

On undersurface 21 of chip body 12, groove 25a is formed in connection to through hole 24a at a position on carbon ink 16a, and groove 25b is formed in connection to through hole 24b at a position on carbon ink 16b. In a state where chip body 12 and film 14 are bonded together, third regions 25a' and 25b' are formed as openings of grooves 25a and 25b are closed by film 14. Third regions 25a' and 25b' are located on carbon inks 16a and 16b. The width of third regions 25a' and 25b' is formed so as to be greater than the width of carbon inks 16a and 16b (see FIG. 4). Third regions 25a' and 25b' are filled with conductive adhesives 26a and 26b (see FIG. 1 and FIG. 4). Thus, it is possible to prevent unbonded portions of chip body 12 and film 14 generated by the thickness of carbon inks 16a and 16b from becoming unexpected channels, to prevent a liquid leaked from first regions 23a' and 23b' from reaching second regions 24a' and 24b'.

FIG. 3A to FIG. 3C are diagrams illustrating the shape of film 14 after printing of carbon inks 16a and 16b. FIG. 3A is a plan view, FIG. 3B is a front view, and FIG. 3C is a left side view.

Film 14 with carbon inks 16a and 16b printed thereon is bonded to undersurface 21 of chip body 12 through adhesion using a transparent organic adhesive, thermo compression bonding or the like so as to cover at least micro-groove 22, through holes 23a, 23b, 24a and 24b and grooves 25a and 25b.

When film 14 is bonded to chip body 12, both ends of carbon ink 16a are located inside first region 23a' and inside second region 24a', and both ends of carbon ink 16b are located inside first region 23b' and inside second region 24b'. Carbon inks 16a and 16b are provided with conductivity and have functions as electrodes.

Electrophoresis by Micro-Channel Chip

First, in micro-channel chip 10, a buffer solution is injected into first region (injection port) 23a' to fill the interior of channel 22'. Next, a sample for analysis is injected. Further, electrode rods 1a and 1b are inserted into second regions 24a' and 24b' to come into contact with conductive adhesives 26a and 26b.

A voltage is applied to both ends of channel 22' as a current flows through electrode rods 1a and 1b. This causes the sample to moves into through channel 22' toward first region (exhaust port) 23b'.

Inside channel 22', the sample is separated according to a different migration speed every molecular weight. A tester can obtain the electrophoresis result by detecting fluorescence intensity.

Effect of Present Embodiment

Figure 4:
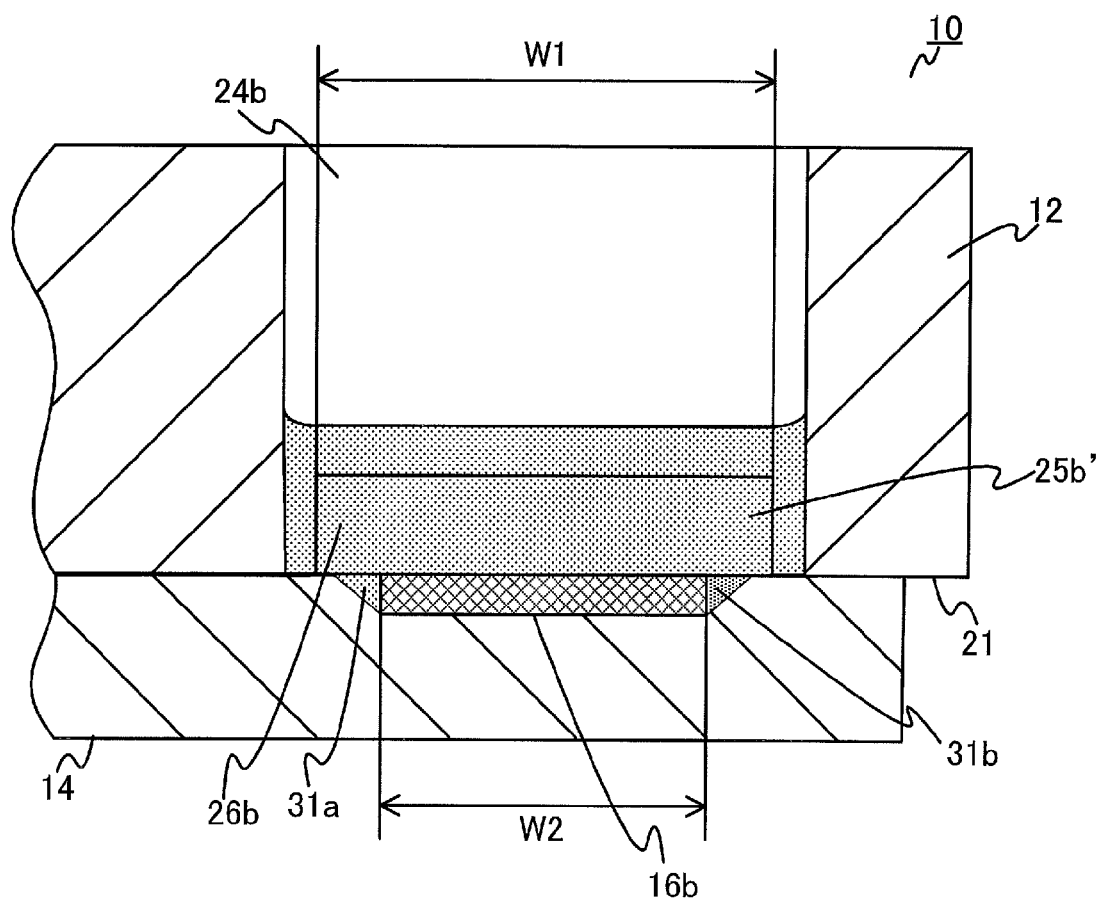
FIG. 4 is an enlarged cross-sectional view along line E-E in FIG. 1A.

FIG. 4 is an enlarged cross-sectional view along line E-E in FIG. 1A. As shown in FIG. 4, the periphery of carbon ink 16b (16a) in film 14 remains unbonded (insufficiently laminated) to chip body 12 due to the thickness of carbon ink 16b (16a), and thus, gaps 31a and 31b may be produced between chip body 12 and film 14 at edges of carbon ink 16a (16b).

Gaps 31a and 31b become unexpected channels that are connected to first region 23b' (23a'). Thus, the liquid (buffer solution and sample) injected into channel 22' of micro-channel chip 10 leaks through gaps 31a and 31b from first region 23b' (23a') by the capillary phenomenon.

Third region 25b' (25a') is formed in micro-channel chip 10 according to the present embodiment. Width W1 of third region 25b' (25a') is formed so as to be greater than width W2 of carbon ink 16b (16a), and thus, third region 25b' (25a') is connected to gaps 31a and 31b. As third region 25b' (25a') is filled with conductive adhesive 26b (26a), openings of gaps 31a and 31b toward third region 25b' (25a') are closed.

Accordingly, the liquid does not move to second region 24a' (24b') from first region 23b' (23a') through gaps 31a and 31b.

As a result, according to the present embodiment, it is possible to prevent the liquid from leaking outward and prevent contamination of the electrodes or external environment.

Variations

Hereinafter, variations of the micro-channel chip according to the present embodiment will be described.

Variation 1

Figure 5A:
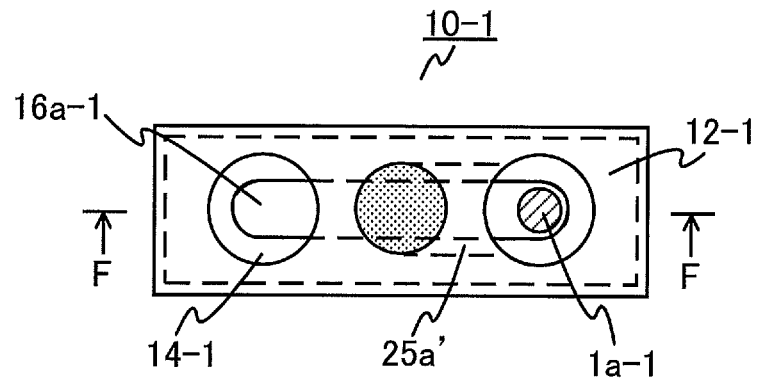
FIG. 5A to FIG. 5C are diagrams illustrating the shape of a micro-channel chip according to an embodiment of the present invention (variation 1)
Figure 5B:
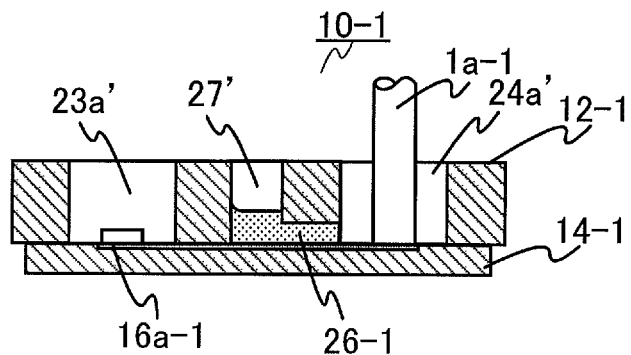
Figure 5C:
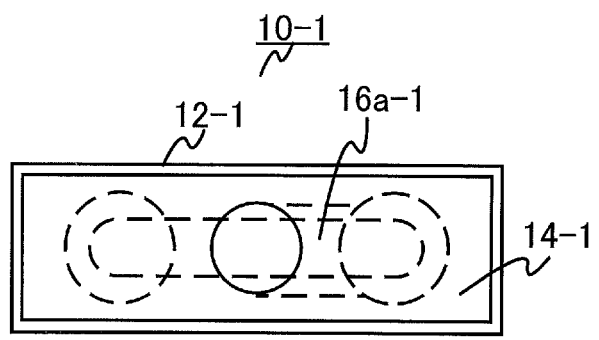

FIG. 5A to FIG. 5C are diagrams illustrating the shape of variation 1 of the micro-channel chip according to the present embodiment. A micro-channel chip 10-1 of variation 1 is used to heat a sample using a heater. FIG. 5A is a plan view, FIG. 5B is a front cross-sectional view along line F-F, and FIG. 5C is a bottom view. FIG. 5A and FIG. 5B show electric heater 1a-1 together. In FIG. 5A to FIG. 5C, parts common to those in FIG. 1A to FIG. 1D are assigned the same reference numerals, and detailed descriptions thereof will be omitted.

Figure 6A:
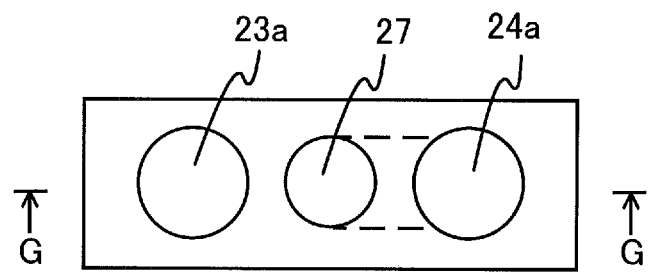
FIG. 6A to FIG. 6C are diagrams illustrating the shape of a chip body of the micro-channel chip shown in FIG. 5A to FIG. 5C.
Figure 6B:
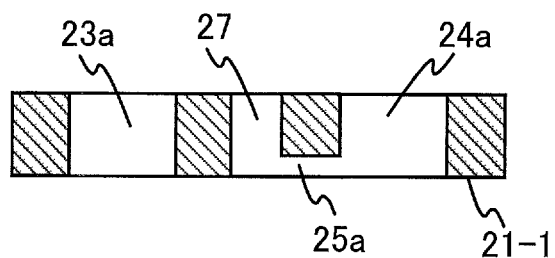
Figure 6C:
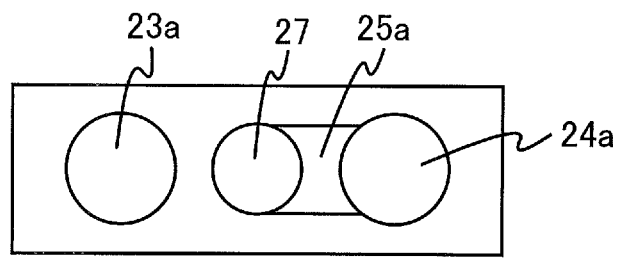

FIG. 6A to FIG. 6C are diagrams illustrating the shape of the chip body of the micro-channel chip shown in FIG. 5A to FIG. 5C. FIG. 6A is a plan view, FIG. 6B is a front cross-sectional view along line G-G, and FIG. 6C is a bottom view. In FIG. 6A to FIG. 6C, parts common to those in FIG. 2A to FIG. 2D are assigned the same reference numerals, and detailed descriptions thereof will be omitted.

Variation 1 is a case where there is only one metal film 16a-1 with an excellent heat transfer property as a transfer function section. In FIG. 5A to FIG. 5C, micro-channel chip 10-1 is configured so that the shapes of chip body 12-1 and film 14-1 are different from those of chip body 12 and film 14 shown in FIG. 1A to FIG. 1D.

Further, in FIG. 6A to FIG. 6C, one through hole 23a, one through hole 24a and one through hole 27 are formed in chip body 12-1. Further, one groove 25a is formed on undersurface 21-1 of chip body 12-1. No micro-groove is formed on chip body 12-1.

In a state where chip body 12-1 and film 14-1 are bonded together, through hole 27 serves as injection port 27' of the adhesive that communicates with third region 25a'. In micro-channel chip 10-1 of variation 1, adhesive 26-1 that fills third region 25a' is injected through injection port 27'. Adhesive 26-1 is introduced into third region 25a' according to the capillary phenomenon, and is stopped at an opening of third region 25a' toward second region 24a' by the capillary phenomenon. Thus, metal film 16a-1 inside second region 24'a is not covered with adhesive 26-1, and thus, it is possible to cause electric heater 1a-1 to be directly contact with metal film 16a-1.

In this manner, adhesive 26-1 that flows in third region 25a' of the channel shape stops its flow at a place where adhesive 26-1 reaches an opening of second region 24a' that is a wide space, and does not cover and hide transfer function section (metal film) 16a-1 in second region 24a'. Since adhesive 26-1 has only to prevent second region 24a' and third region 25a' from communicating with each other and need not have the transfer function, it is possible to increase the degree of freedom for selection.

According to variation 1, similarly, the liquid leaked from first region 23'a is stopped in third region 25'a, and can be prevented from reaching second region 24a'. As a result, it is possible to prevent the liquid from leaking, to prevent contamination of an external environment, and to safely heat the sample injected into first region 23a' using electric heater 1a-1.

In the above embodiment, a case where carbon inks 16a and 16b are used as conductive members and metal film 16a-1 is used as a heat transfer member has been described, but the present invention is not limited thereto. That is, other conductive members and heat transfer members may be used to achieve the same effect.

Further, in the above embodiment, a case where film 14 is bonded to chip body 12 has been described, but the present invention is not limited thereto. For example, as shown in FIG. 1 of PTL 1, a thin plate may be bonded to a chip body to achieve the same effect.

According to the present invention, as described in the above embodiment, the space (third region) that communicates with gaps (unexpected channels) that may be produced at edges of the transfer function section is formed between the space (first region) into which the liquid is introduced and the space (second region) electrically or thermally connected thereto via the transfer function section, and the third region is filled with the adhesive. Accordingly, it is possible to prevent the liquid introduced into the first region from leaking out to the space of the second region. As long as this effect can be achieved, the shape of the groove of the substrate member for formation of the first region and the second region is not limited to the shape shown in the above embodiment. The first region may be a space in the middle of a flow passage.

This application is entitled and claims the benefit of Japanese Patent Application No. 2011-082820, filed on Apr. 4, 2011, the disclosure of which including the specification, drawings and abstract is incorporated herein by reference in its entirety.

INDUSTRIAL APPLICABILITY

The fluid handling apparatus and the fluid handling system according to the present invention can be used for an apparatus that carries out an inspection/analysis of trace substances accurately and at high speed in the scientific field such as biochemistry and analytical chemistry or in the medical field.

REFERENCE SIGNS LIST

10 Micro-channel chip
12, 12-1 Chip body
14, 14-1 Film
16a, 16b Carbon ink
16a-1 Metal film
22 Micro-groove
22' Channel
23a, 23b, 24a, 24b, 27 Through hole
23a', 23b', 26' First region
24a', 24b' Second region
25a, 25b Groove
25a', 25b' Third region
26a', 26b', 26-1 Adhesive
27' Injection port

The invention claimed is:
1. A fluid handling apparatus comprising:
 a substrate member where a groove or a through hole is formed;
 a cover member that is bonded to one surface of the substrate member and has a thin film shape or a thin plate shape; and
 a transfer function section that is formed in a laminated shape to cover a part of a surface of the cover member on a side of the substrate member and transfers electricity or heat,
 wherein a groove or a through hole that forms a first region is formed in a portion of the substrate member corresponding to one end of the transfer function section,
 wherein an opening of the groove or the through hole that forms the first region on a side of the cover member is closed by the cover member,
 wherein a second region that communicates with an outside is formed in a portion of the substrate member corresponding to the other end of the transfer function section,
 wherein the second region is configured for insertion of an electrode rod or electric heater, the electrode rod or electric heater adapted to electrically or thermally connect to the transfer function section;

wherein the transfer function section is disposed between the substrate member and the cover member, and electrically or thermally connects the first region and the second region to each other, wherein a groove that forms a third region is formed on the side of the cover member of the substrate member, the groove that forms the third region being formed in a portion of the substrate member corresponding to a portion between one end of the transfer function section corresponding to the first region and the other end of the transfer function section corresponding to the second region to extend over edges of the transfer function section, wherein an opening of the groove that forms the third region on the side of the cover member is closed by the cover member, and wherein the third region communicates with the second region, the third region being filled with an adhesive, wherein the adhesive is configured to prevent liquid from leaking out from the first region, thereby preventing fluid communication between the first and second regions, and wherein when the adhesive is disposed in the second region, the adhesive is adapted to contact the electrode rod or the electric heater inserted into the second region.

2. The fluid handling apparatus according to claim 1,
wherein the adhesive has conductivity or a heat transfer property.

3. A fluid handling system comprising the fluid handling apparatus according to claim 1.

* * * * *